US00PP09527P

United States Patent [19]

Austin

[11] Patent Number: Plant 9,527

[45] Date of Patent: Apr. 30, 1996

[54] SHRUB ROSE PLANT NAMED 'AUSMUM'

[75] Inventor: David C. H. Austin, Albrighton, England

[73] Assignee: David Austin Roses Limited, England

[21] Appl. No.: 457,999

[22] Filed: Jun. 1, 1995

[30] Foreign Application Priority Data

Nov. 4, 1994 [GB] United Kingdom ..... AFP5/1620

[51] Int. Cl.[6] ..... A01H 5/00

[52] U.S. Cl. ..... Plt./1

[58] Field of Search ..... Plt./1, 22

*Primary Examiner*—Howard J. Locker

*Attorney, Agent, or Firm*—Klarquist Sparkman Campbell Leigh & Whinston

[57] ABSTRACT

A repeat flowering shrub rose of good branching habit having golden yellow and apricot colored old-fashioned shaped flowers and dark foliage.

1 Drawing Sheet

The present invention relates to a new and distinct variety of rose shrub plant which was originated by me by crossing the variety Graham Thomas, not patented, with the variety Abraham Darby, U.S. Plant Pat. No. 7,215.

The primary objective of this breeding was to produce a new shrub rose variety having golden yellow and apricot colored old-fashioned shaped flowers, with repeat flowering and disease resistance. The objective was substantially achieved, along with other desirable improvements, as evidenced by the following unique combination of characteristics that are outstanding in the new variety and that distinguish it from its parents, as well as from all other varieties of which I am aware:

1. The inside of the petals is copper colored and the outside is a paler copper-yellow.
2. Dark foliage.
3. Good branching habit.

Asexual reproduction of this new variety by budding, as performed at Albrighton, Wolverhampton, England, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated. Society (London) Colour Chart, except where ordinary dictionary significnace of color is indicated.

Parentage:

*Seed parent.*—Graham Thomas.

*Pollen parent.*—Abraham Darby.

Classification:

*Botanical.*—*Rosa hybrida.*

*Commercial.*—Shrub.

FLOWER

Observations made from specimens grown in a garden/greenhouse environment at Albrighton, Wolverhampton, England, in July 1993.

Blooming habit: Recurrent.

Bud:

*Size.*—About 1.5–1.75 inches long when the petals start to unfurl.

*Form.*—The bud form is long, pointed ovoid.

*Color.*—When sepals first divide, bud color is Greyed-Purple Group 185A. When half blown, the upper sides of the petals are Orange-Red Group 30C/Orange-Red Group 33B; and the lower sides of the petals are Yellow-Orange Group 21C.

*Sepals.*—Color: The major color is Yellow-Green Group 144A/B; the base is Greyed-Purple Group 185A. Surface texture: Rough. There are three normally to heavily appendaged sepals. There are two unappendaged sepals with smooth, slightly hairy edges.

*Receptacle.*—Color: Yellow-Green 144A/B with Greyed-Purple Group 185A blush. Shape: Goblet. Size: Medium, about 0.4 inches ×0.3 inches. Surface: Slightly pimply.

*Peduncle.*—Length: Medium to short (very variable), averaging about 1–3 inches. Surface: Prickly. Color: Light green. Strength: Slightly bending, slender.

Bloom:

*Size.*—Large to medium. Average open size is about 3–4 inches.

*Borne.*—Singly or several together. If in clusters: 1–5 per stem, irregular shape.

*Stems.*—Medium, normal. Average length is about 24 inches.

*Form.*—When first open: Loose to open cupped. Permanence: Form becomes looser and more open to the end. Petal size increases markedly with age and outer petals curl back.

*Petalage.*—Number of petals under normal conditions: 50.

*Color.*—The upper side of the outer petals is Orange Group 29B, middle petals are Orange-Red Group 32B and inner petals deepen to Orange-Red Group 33B. The reverse side of the petals is Yellow-Orange Group 21C. The basal one-quarter of petals is Yellow-Orange Group 14B. The major color on the upper side is Orange-Red Group 32B.

*Variegations.*—None.

*Discoloration.*—The general tonality at the end of the first day: Slightly paler. At the end of the third day: Paler, less orange and more pink, tending to Red Group 37A/B.

*Fragrance.*—Moderate.

Petals:

*Texture.*—Fairly thick, smooth.

*Shape.*—Notched or undulating, deltoid, heart-shaped. Outer petals broad, almost round; inner petals narrower and ovoid.

*Form.*—Tips slightly recurved, outer petal edges slightly quilled.

*Arrangement.*—Informal, with a few large petaloids in the center.

*Persistence.*—Petals drop off cleanly before drying.

*Lastingness.*—On the plant: Long, about 5–7 days. As a cut flower: Not tested.

Reproductive parts:

*Anthers.*—Size: Medium. Quantity: Many. Color: Yellow. Arrangement: Regular around styles, rarely tucked in calyx or party so.

*Filaments.*—Color: Reddish or deep Orange-Red Group 33A.

*Pollen.*—Color: Gold yellow.

*Styles.*—Color: Base is greenish white, top half has streak of Red-Purple Group 58B.

*Stigmas.*—Color: Yellow.

Form: Shrub.

Growth: Vigorous, upright, branching. Mature plant is about 4 feet tall and 3.5 feet wide.

Foliage:

*Number of leaflets on normal mid-stem leaves.*—5.

*Size.*—Large, about 7 inches long ×5.5 inches wide.

*Quantity.*—Abundant.

*Color.*—New foliage: Yellow-Green Group 146A and margin is Greyed-Red Group 183A. Old foliage: Yellow-Green Group 147A.

Leaflets:

*Shape.*—Oval with a pointed apex.

*Texture.*—Upper side: Glossy, smooth.

*Edge.*—Serrated.

*Serration.*—Single.

*Petiole rachis.*—Color: Green, slightly reddish.

*Petiole underside.*—1–3 prickles per internode.

*Stipules.*—Long to medium, serrated, about 1–2 inches long.

*Disease resistance.*—Resistant to mildew and blackspot under normal growing conditions at Arbrighton, Wolverhampton, England.

Wood:

*New wood.*—Color: Reddish. Bark: Smooth.

*Old wood.*—Color; Brown, streaky. Bark: Rough.

Prickles:

*Quantity.*—On main canes from base: Ordinary. On laterals from main canes: Ordinary.

*Form.*—Long to medium with broad base, slightly hooked downward.

*Color when young.*—Red.

*Position.*—Evenly distributed around stem.

Small prickles:

*Quantity.*—On main stalks: None. On laterals: None.

I claim:

1. A new and distinct variety of rose plant of the shrub class, substantially as herein shown and described, characterized particularly as to novelty by the unique combination of its petals having a copper color on the inside and a paler copper-yellow on the outside, dark foliage and good branching habit.

* * * * *

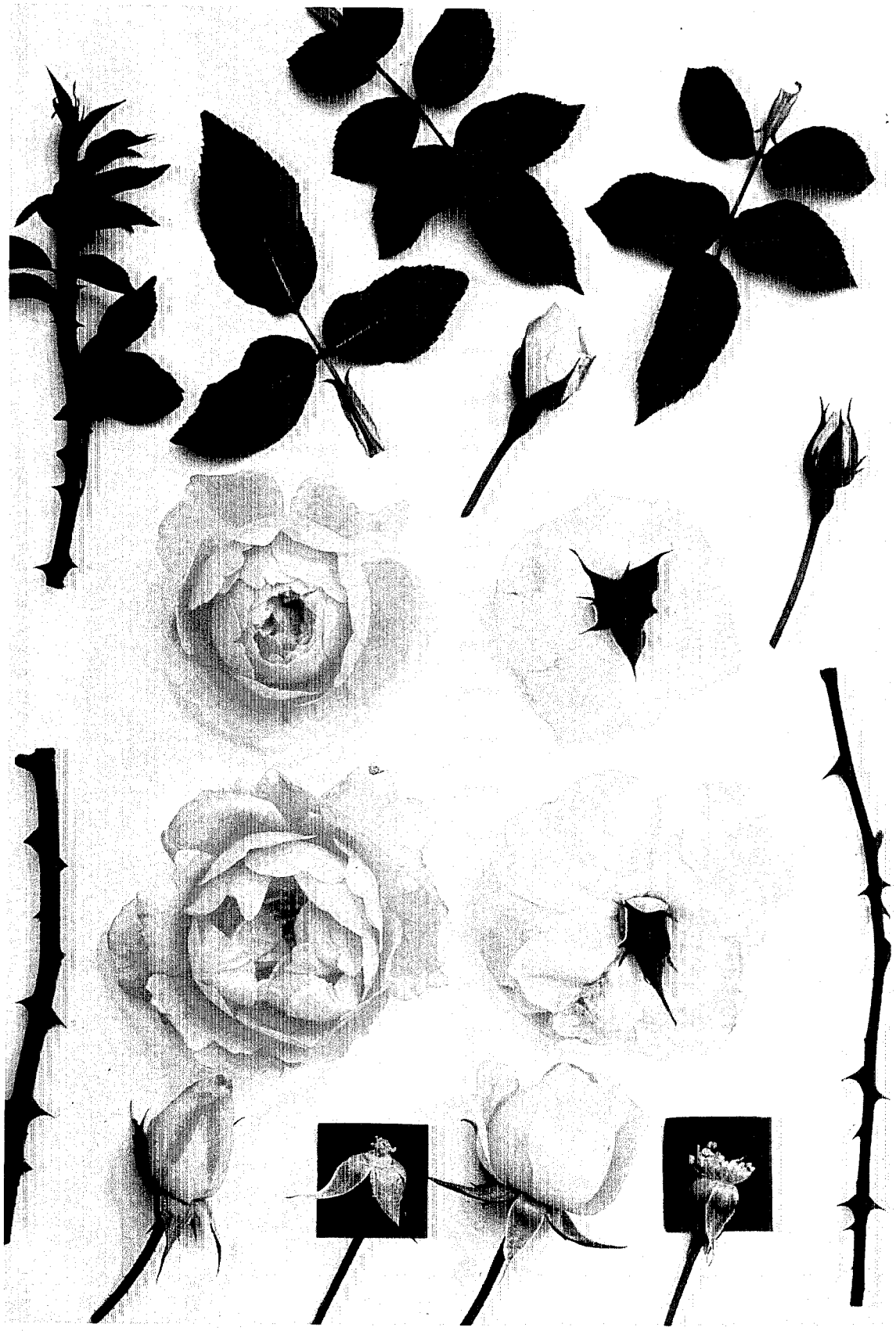

UNITED STATES PATENT AND TRADEMARK OFFICE

CERTIFICATE OF CORRECTION

PATENT NO. : PP09527

DATED : April 30, 1996

INVENTOR(S) : David C. H. Austin

It is certified that error appears in the above-indentified patent and that said Letters Patent is hereby corrected as shown below:

Col. 1, lines 32-33; after first occurrence of "indicated.", delete all to end of paragraph.

Col. 2, line 15; change "inches x0.3 inches." to "inches x 0.3 inches."

Col. 2, line 18, after "Light green" insert --and bronzy--.

Col. 3, line 11, change "party" to --partly.

Col. 3, line 19, delete "vigorous, upright, branching", and insert in place thereof --Vigorous, branching and rounded--.

Col. 3, line 23, change "long x5.5 inches" to --long x 5.5 inches--.

UNITED STATES PATENT AND TRADEMARK OFFICE

CERTIFICATE OF CORRECTION

PATENT NO. : PP09527

DATED : April 30, 1996

INVENTOR(S) : David C. H. Austin

It is certified that error appears in the above-indentified patent and that said Letters Patent is hereby corrected as shown below:

Col 4, line 8; change "Arbrighton" to --Albrighton--.

Col. 4, line 12; change "Color; Brown" to --Color: Brown--.

Signed and Sealed this

Fourth Day of March, 1997

*Attest:*

*Attesting Officer*

BRUCE LEHMAN

*Commissioner of Patents and Trademarks*